(12) United States Patent
Miwa et al.

(10) Patent No.: US 9,751,907 B2
(45) Date of Patent: Sep. 5, 2017

(54) ARBEKACIN DERIVATIVE, AND PRODUCTION AND USE THEREOF

(71) Applicant: MEIJI SEIKA PHARMA CO., LTD., Tokyo (JP)

(72) Inventors: Hiroyasu Miwa, Tokyo (JP); Hisashi Kishi, Kitakami (JP); Toshiro Sasaki, Odawara (JP); Takashi Murata, Yokohama (JP); Makoto Oyama, Kyobashi (JP); Nao Sano, Odawara (JP); Ayako Odagiri, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/891,838

(22) PCT Filed: May 29, 2014

(86) PCT No.: PCT/JP2014/064221
§ 371 (c)(1),
(2) Date: Nov. 17, 2015

(87) PCT Pub. No.: WO2014/192848
PCT Pub. Date: Dec. 4, 2014

(65) Prior Publication Data
US 2016/0096859 A1    Apr. 7, 2016

(30) Foreign Application Priority Data
May 30, 2013  (JP) ................................ 2013-114597

(51) Int. Cl.
*C07H 15/234*    (2006.01)
(52) U.S. Cl.
CPC ................................ *C07H 15/234* (2013.01)
(58) Field of Classification Search
None
See application file for complete search history.

(56) References Cited

U.S. PATENT DOCUMENTS

| | | | |
|---|---|---|---|
| 4,001,208 A | 1/1977 | Umezawa et al. |
| 4,107,424 A | 8/1978 | Umezawa et al. |
| 4,170,642 A | 10/1979 | Umezawa et al. |
| 2007/0161581 A1 | 7/2007 | Minowa et al. |
| 2009/0186841 A1 | 7/2009 | Kobayashi et al. |
| 2012/0165283 A1 | 6/2012 | Kobayashi et al. |

FOREIGN PATENT DOCUMENTS

| | | |
|---|---|---|
| EP | 2567691 A1 | 3/2013 |
| JP | 52-33629 B2 | 8/1977 |
| JP | 63-32799 B2 | 7/1988 |
| JP | 9-104694 A | 4/1997 |
| WO | 2005/070945 A1 | 8/2005 |
| WO | 2007/142150 A1 | 12/2007 |

OTHER PUBLICATIONS

Shinichi Kondo, "Synthesis of 1-N-{(S)-4-amino-2-hydroxybutyryl}-kanamycin B and -3',4'-dideoxykanamycin B active against kanamycin-resistant bacteria", The Journal of Antibiotics, Jul. 1973, pp. 412-415, vol. 26.
Shinichi Kondo, Development of arbekacin and synthesis of new derivatives stable to enzymic modifications by methicillin-resistant *Staphylococcus aureus*, Japanese Journal of Antibiotics, Jun. 1994, pp. 561-574, vol. 47, No. 6.
Shinichi Kondo, et al., "Synthesis of 2"-amino-2"-deoxyarbekacin and its analogs having potent activity against methicillin-resistant *Staphylococcus aureus*", Journal of Antibiotics, 1994, pp. 821-832, vol. 47, No. 7.
Shinichi Kondo, et al., "Structures of enzymatically modified products of arbekacin by methicillin-resistant *Staphylococcus aureus*", Journal of Antibiotics, Feb. 1993, pp. 310-315, vol. 46, No. 2.
Kunimoto Hotta, et al., "The Novel Enzymatic 3"-N-Acetylation of Arbekacin by an Aminoglycoside 3-N-Acetyltransferase of Streptomyces Origin and the Resulting Activity", Journal of Antibiotics, 1998, pp. 735-742, vol. 51, No. 8.
Yukiko Hiraiwa, et al., "Synthesis and antibacterial activity of 5-deoxy-5-episubstituted arbekacin derivatives", Bioorganic & Medicinal Chemistry Letters, 2007, pp. 3540-3543, vol. 17, No. 13.
International Search Report for PCT/JP2014/064221 dated Jun. 24, 2014 [PCT/ISA/210].
Written Opinion for PCT/JP2014/064221 dated Jun. 24, 2014 [PCT/ISA/237].
International Preliminary Report on Patentability issued from the International Bureau in counterpart International Application No. PCT/JP2014/064221, mailed on Dec. 10, 2015.
Extended European Search Report dated Oct. 24, 2016, issued from the European Patent Office in corresponding European Application No. 14803509.0.
Shinichi Konda "Synthesis of 1-N-{(S)-4-Amino-2-Hydroxybutyryl}-Kanamycin B and -3', 4'-Dideoxykanamycin B Active Against Kanamycin-Resistant Bacteria," The Journal of Antibiotics, vol. 26 No. 7; Jul. 1973; pp. 412-415.

*Primary Examiner* — Layla Berry
(74) *Attorney, Agent, or Firm* — Sughrue Mion, PLLC

(57) ABSTRACT

It has been found that adding carbon dioxide or the like to a solution containing arbekacin free base makes it possible to produce arbekacin derivatives including arbekacin carbonate and carbamic acid of arbekacin. Moreover, it has been found that the arbekacin derivatives have a high stability, and that the use thereof enables efficient productions of highly-pure arbekacin free base and pharmaceutically acceptable salt thereof.

8 Claims, 5 Drawing Sheets

ARBEKACIN FREE BASE + SODIUM CARBONATE (15 eq.)

ARBEKACIN FREE BASE + SODIUM CARBONATE (3 eq.)

ARBEKACIN FREE BASE

ARBEKACIN DERIVATIVE, AND PRODUCTION AND USE THEREOF

CROSS REFERENCE TO RELATED APPLICATIONS

This application is a National Stage of International Application No. PCT/JP2014/064221, filed on May 29, 2014, which claims priority from Japanese Patent Application No. 2013-114597, filed on May 30, 2013, the contents of all of which are incorporated herein by reference in their entirety.

TECHNICAL FIELD

The present invention relates to an arbekacin derivative, and the production and use thereof.

BACKGROUND ART

Arbekacin (free base) is a compound having the following structure, and a sulfate thereof is used for the treatment of pneumonia and sepsis caused by methicillin-resistant *Staphylococcus aureus*.

[Chem. 1]

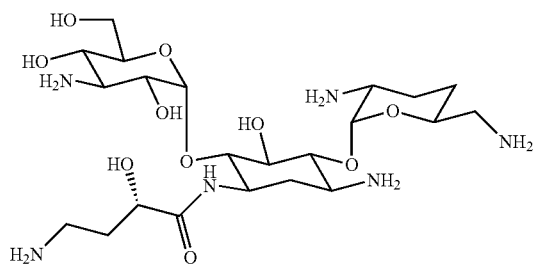

A general method for arbekacin sulfate normally uses arbekacin free base synthesized by a method described in Japanese Examined Patent Application Publication No. Sho 52-33629 (PTL 1) or the like, and includes adding sulfuric acid to an aqueous solution of the arbekacin free base, followed by freeze-drying to obtain the arbekacin sulfate in a solid form. In this case, the synthesized arbekacin free base is purified by chromatography. However, this method is not efficient because improving the purity generally requires a large amount of a resin, requires related substances to be removed by changing the eluent concentration stepwise, requires a large amount of the eluent, requires a long time to carry out the procedure, and requires other things. In addition, the arbekacin sulfate obtained by this method unavoidably contains approximately 1 to 2% of related substances such as dibekacin.

Arbekacin can also be used as arbekacin free base without being converted into a pharmaceutically acceptable salt such as a sulfate. Moreover, it is also possible to convert arbekacin free base to pharmaceutically acceptable salts other than sulfate for use. Nevertheless, arbekacin free base is likely to degrade, particularly, degrade at position 1''', so that dibekacin is formed as illustrated in the following equation. For this reason, arbekacin free base needs to be stored at low temperature, which is industrially disadvantageous.

[Chem. 2]

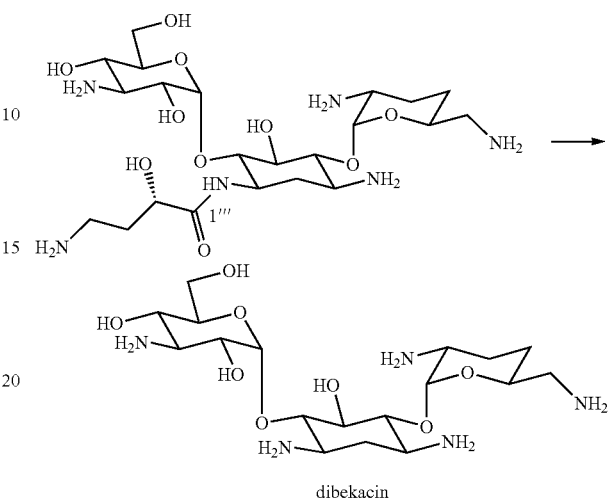

dibekacin

Note that Japanese Examined Patent Application Publication No. Sho 63-32799 (PTL 2) and The Journal of Antibiotics, vol. 26, 1973, p. 412 (NPL 1) state that the crude arbekacin free base obtained by reactions is purified by chromatography and concentrated to dryness to thus obtain arbekacin dicarbonate. However, in these methods, arbekacin carbonate is unintentionally formed during concentration of the solution resulting from purification of arbekacin free base by chromatography. And this arbekacin dicarbonate is obtained by drying without performing a purification step. Hence, the methods do not include intentionally forming arbekacin carbonate and purifying it by isolation. Furthermore, these literatures do not disclose carbamic acid of arbekacin or arbekacin derivatives.

CITATION LIST

Patent Literatures

[PTL 1] Japanese Examined Patent Application Publication No. Sho 52-33629
[PTL 2] Japanese Examined Patent Application Publication No. Sho 63-32799

Non Patent Literature

[NPL 1] The Journal of Antibiotics, vol. 26, 1973, p. 412

SUMMARY OF INVENTION

Technical Problem

An object of the present invention is to provide a highly stable arbekacin derivative convertible to arbekacin free base or a pharmaceutically acceptable salt thereof, and a production method for the arbekacin derivative. Another object of the present invention is to provide a method for producing arbekacin free base more efficiently with a higher purity via the arbekacin derivative than in a case of chromatographic purification. A further object of the present invention is to provide a method for producing a pharmaceutically acceptable salt of arbekacin efficiently with a high purity by using the arbekacin derivative.

Solution to Problem

As a result of earnest studies, the present inventors have found that adding carbon dioxide, a carbonate, or a hydrogen carbonate to a solution containing arbekacin free base forms a carbamic acid of arbekacin together with arbekacin carbonate in the solution, and by precipitating and separating the resultant, arbekacin derivatives including arbekacin carbonate and carbamic acid of arbekacin (refereed to as "carbamic acid derivative of arbekacin including arbekacin carbonate") are obtained in the solid form. Moreover, the present inventors have found that the carbamic acid derivative of arbekacin including arbekacin carbonate obtained by separating the precipitate: (i) has a purity increased as a result of removal of related substances contained in the original arbekacin free base; (ii) is more stable than arbekacin free base; (iii) readily loses carbon dioxide (carbon dioxide gas) by a chromatographic method and is convertible to highly-pure arbekacin free base; and (iv), as in the case of arbekacin free base, by adding an acid to a solution of the carbamic acid derivative of arbekacin including arbekacin carbonate, readily loses carbon dioxide (carbon dioxide gas), and is convertible to a highly-pure pharmaceutically acceptable salt of arbekacin. FIG. 1 shows the outline of the above. In FIG. 1, at least one of $R_1$, $R_2$, $R_3$, and $R_4$ is a carboxyl group (COOH), while the rest represent hydrogen atoms (H), and x and y each independently represent the number from 1 to 5.

Specifically, the present invention provides the following.

[1] A production method for a carbamic acid derivative of arbekacin represented by the following formula (2):

[Chem. 4]

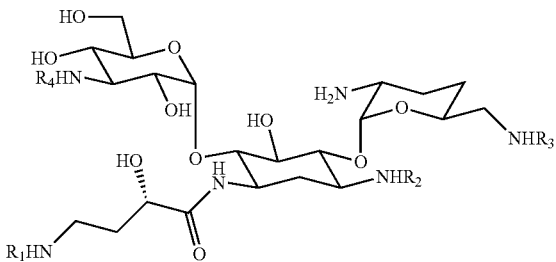

Formula (2)

[in the formula, at least one of $R_1$, $R_2$, $R_3$, and $R_4$ is COOH, while the rest represent H] and including arbekacin carbonate represented by the following formula (1):

[Chem. 3]

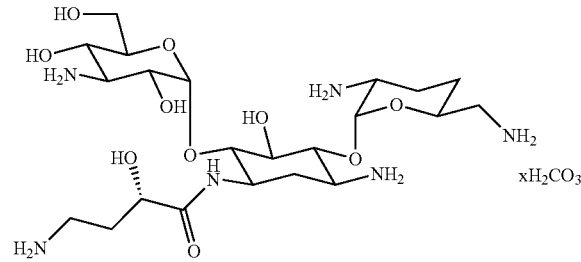

Formula (1)

[in the formula, x represents 1 to 5], the production method comprising:

(a) a step of adding any one of carbon dioxide, a carbonate, and a hydrogen carbonate to a solution containing arbekacin free base, thereby preparing a solution containing a carbamic acid derivative of arbekacin including arbekacin carbonate;

(b) a step of precipitating the carbamic acid derivative of arbekacin including arbekacin carbonate in the solution; and (c) a step of separating the precipitating carbamic acid derivative of arbekacin including arbekacin carbonate.

[2] The production method according to [1], wherein, in the step (a), carbon dioxide is added to the solution containing arbekacin free base to make a pH from 6.1 to 10.5, thereby preparing the solution containing the carbamic acid derivative of arbekacin including arbekacin carbonate.

[3] The production method according to [1], wherein, in the step (a), anyone of a carbonate and a hydrogen carbonate in an amount of 0.5 equivalents or more is added to the solution containing arbekacin free base, thereby preparing the solution containing the carbamic acid derivative of arbekacin including arbekacin carbonate.

[4] The production method according to any one of [1] to [3], wherein, in the step (b), the solution prepared in the step (a) is mixed with an organic solvent, thereby precipitating the carbamic acid derivative of arbekacin including arbekacin carbonate.

[5] The production method according to [4], wherein the organic solvent used in the step (b) is selected from the group consisting of methanol, ethanol, propanol, dimethyl sulfoxide, acetonitrile, pyridine, tetrahydrofuran, acetone, N,N-dimethylformamide, and solvent combinations thereof.

[6] A carbamic acid derivative of arbekacin including arbekacin carbonate, produced by the method according to any one of [1] to [5].

[7] A production method for arbekacin free base having a related substance content of 0.5% or less, the production method comprising a step of removing carbon dioxide from the carbamic acid derivative of arbekacin including arbekacin carbonate according to [6].

[8] A production method for a pharmaceutically acceptable salt of arbekacin, the production method comprising a step of adding an acid to the carbamic acid derivative of arbekacin including arbekacin carbonate according to [6], the pharmaceutically acceptable salt having a related substance content of 0.5% or less, and represented by the following formula (3):

[Chem. 5]

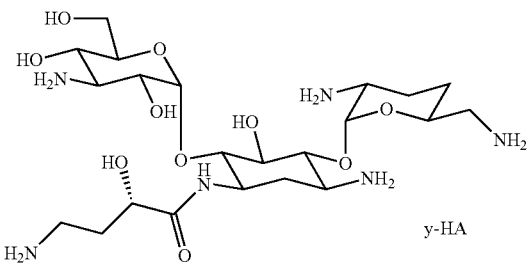

Formula (3)

[in the formula, y represents 1 to 5, and HA represents a pharmaceutically acceptable acid].

[9] Arbekacin free base produced by the method according to [7], and having a related substance content of 0.5% or less.

[10] A pharmaceutically acceptable salt of arbekacin, produced by the method according to [8], and having a related substance content of 0.50 or less.

[11] A production method for arbekacin free base having a related substance content of 0.5% or less, the production method comprising:

a step of producing a carbamic acid derivative of arbekacin including arbekacin carbonate by the method according to any one of [1] to [5]; and a step of removing carbon dioxide from the carbamic acid derivative of arbekacin including arbekacin carbonate.

[12] A production method for a pharmaceutically acceptable salt of arbekacin, the production method comprising:

a step of producing an carbamic acid derivative of arbekacin including arbekacin carbonate by the method according to any one of [1] to [5]; and a step of adding an acid to the carbamic acid derivative of arbekacin including arbekacin carbonate, wherein the pharmaceutically acceptable salt has a related substance content of 0.50 or less.

Advantageous Effects of Invention

The methods of the present invention make it possible to readily remove related substances by converting arbekacin free base to a carbamic acid derivative of arbekacin including arbekacin carbonate, and precipitating and separating the resultant, without using a method for purifying arbekacin free base by chromatography.

The carbamic acid derivative of arbekacin including arbekacin carbonate obtained according to the present invention is in the solid form having a high stability and low moisture-absorbing properties in comparison with arbekacin free base. Thus, it is possible to easily store the carbamic acid derivative of arbekacin including arbekacin carbonate as raw materials of arbekacin free base and a pharmaceutically acceptable salt of arbekacin.

Further, arbekacin free base needs to be solidified by freeze-drying or spray-drying an aqueous solution thereof. In contrast, the carbamic acid derivative of arbekacin including arbekacin carbonate obtained according to the present invention is precipitated in the reaction solution, separated by a common, easier method (for example, filtration) using neither freeze-drying nor spray-drying, and then dried, so that the solids can be obtained. Moreover, the purification is possible by any purification method known to those skilled in the art without relying on chromatography. Accordingly, the carbamic acid derivative of arbekacin including arbekacin carbonate is industrially advantageous, too.

Furthermore, the carbamic acid derivative of arbekacin including arbekacin carbonate obtained according to the present invention readily loses a carbon dioxide gas by being mixed with an acid, and forms a pharmaceutically acceptable salt (for example, arbekacin sulfate). Thus, from this point also, the carbamic acid derivative of arbekacin including arbekacin carbonate is advantageous as the raw material of a pharmaceutically acceptable salt of arbekacin.

DESCRIPTION OF EMBODIMENTS

Figure 1:
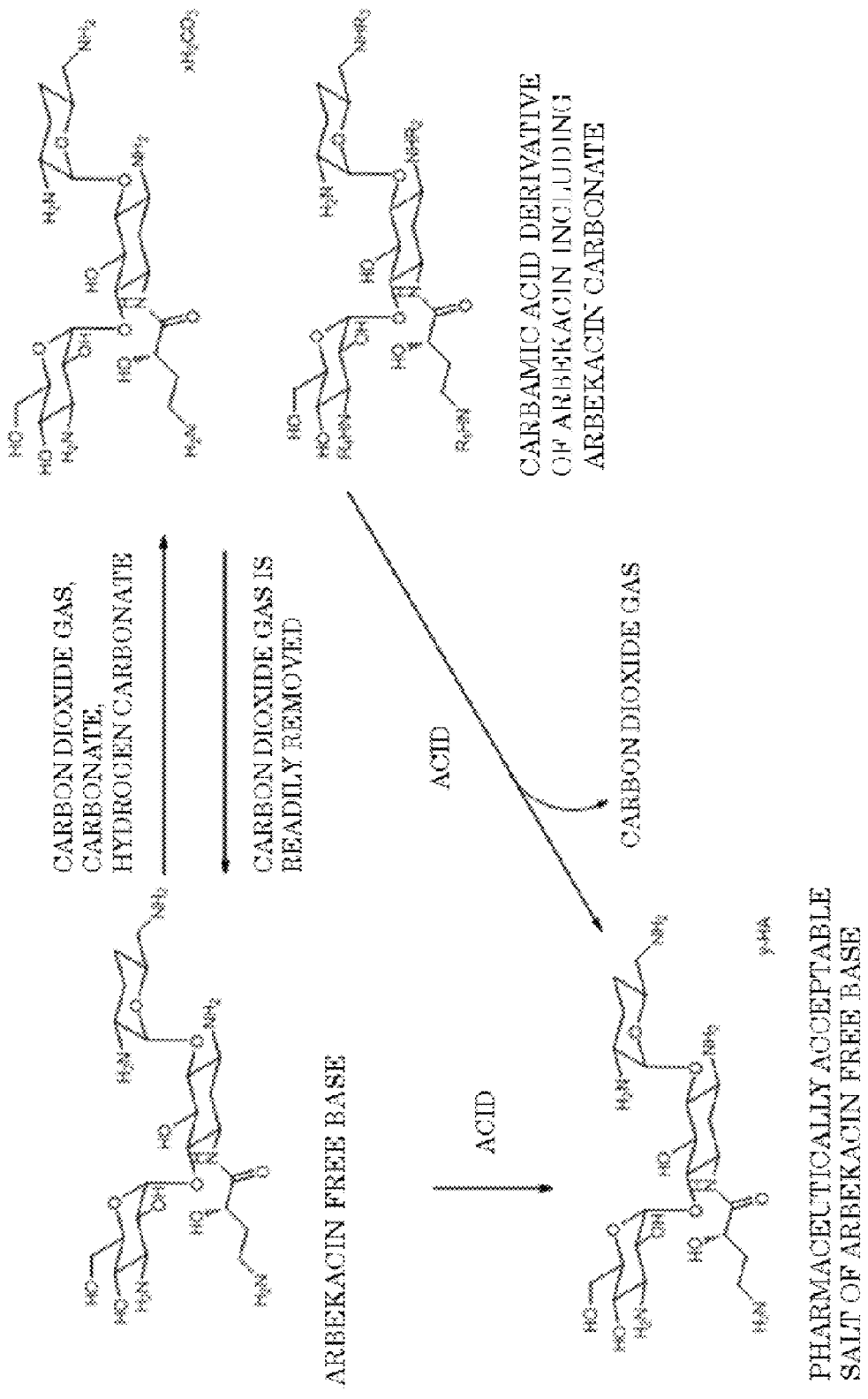
FIG. 1 is a figure showing a schematic of the characteristics, production method, and use of a carbamic acid derivative of arbekacin including arbekacin carbonate of the present invention.

<Production Method for Carbamic Acid Derivative of Arbekacin Including Arbekacin Carbonate>

The present invention provides a production method for a carbamic acid derivative of arbekacin represented by the following formula (2):

[Chem. 7]

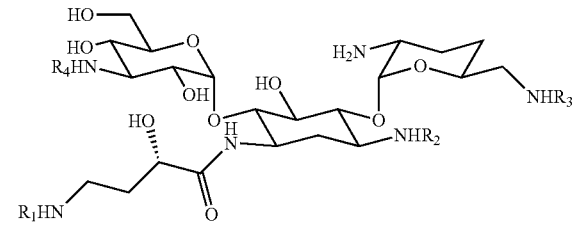

Formula (2)

[in the formula, at least one of $R_1$, $R_2$, $R_3$, and $R_4$ is COOH, while the rest represent H] and including arbekacin carbonate represented by the following formula (1):

[Chem. 6]

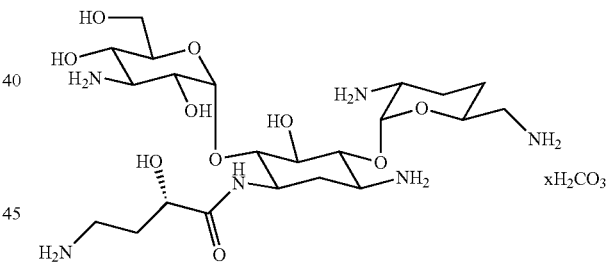

Formula (1)

[in the formula, x represents 1 to 5], the production method comprising:

(a) a step of adding any one of carbon dioxide, a carbonate, and a hydrogen carbonate to a solution containing arbekacin free base, thereby preparing a solution containing a carbamic acid derivative of arbekacin including arbekacin carbonate;

(b) a step of precipitating the carbamic acid derivative of arbekacin including arbekacin carbonate in the solution; and (c) a step of separating the precipitated carbamic acid derivative of arbekacin including arbekacin carbonate. Note that, in the present invention, the term "arbekacin carbonate" according to the present invention includes arbekacin carbonate containing a carbonate ion represented by $CO_3^{2-}$ and arbekacin carbonate containing a hydrogen carbonate ion represented by $HCO_3^-$ (i.e., arbekacin hydrogen carbonate).

—In Case of Using Carbon Dioxide—

In the case where carbon dioxide is added to the solution containing arbekacin free base in the step (a), a solvent to be used should be such that the arbekacin free base can be dissolved therein. It is possible to use water, or a solvent mixture of water with methanol, ethanol, propanol, dimethyl sulfoxide, acetonitrile, pyridine, tetrahydrofuran, acetone, or N,N-dimethylformamide. Water is preferable. The amount of the solvent used is not particularly limited, as long as the amount allows the dissolution of the raw material arbekacin free base. Nevertheless, the amount is preferably 1.6-fold to 200-fold more than that of the arbekacin free base. When carbon dioxide is blown into the solution containing arbekacin free base, the temperature is not particularly limited, and the blowing can be carried out at any temperature. The temperature is preferably 0 to 30° C.

When carbon dioxide is blown into the solution containing arbekacin free base to form a carbamic acid derivative of arbekacin including arbekacin carbonate, the pH is preferably 6.1 to 10.5, further preferably 7.5 to 9.0. This makes it possible to prepare a solution containing arbekacin derivatives including arbekacin carbonate represented by the formula (1) and carbamic acid of arbekacin represented by the formula (2) (i.e., carbamic acid derivative of arbekacin including arbekacin carbonate). Note that in the case where carbon dioxide is added to the solution containing arbekacin free base as described above, arbekacin carbonate containing a hydrogen carbonate ion represented by $HCO_3^-$ (i.e., arbekacin hydrogen carbonate) is obtained as the arbekacin carbonate.

In the case where the solvent used in the step (a) is a mixture solution of water with an organic solvent, the blowing of carbon dioxide can precipitate the carbamic acid derivative of arbekacin including arbekacin carbonate in the solution without further adding any organic solvent (i.e., can form a slurry solution). In this case, the step (a) and the step (b) constitute one inseparable step.

On the other hand, in the case where water is used as the solvent in the step (a), even when carbon dioxide is blown, the carbamic acid derivative of arbekacin including arbekacin carbonate does not precipitate in the solution. For this reason, in the step (b), the solution prepared in the step (a) is mixed with an organic solvent, thereby precipitating the carbamic acid derivative of arbekacin including arbekacin carbonate. In this case, the organic solvent to be used is not particularly limited, as long as the carbamic acid derivative of arbekacin including arbekacin carbonate can be precipitated. Nevertheless, the organic solvent is preferably one or a solvent mixture selected from the group consisting of methanol, ethanol, propanol, dimethyl sulfoxide, acetonitrile, pyridine, tetrahydrofuran, acetone, and N,N-dimethylformamide. Methanol or ethanol is further preferable. The amount of the solvent used is not particularly limited, as long as the amount allows the precipitation of the carbamic acid derivative of arbekacin including arbekacin carbonate. Nevertheless, the amount is preferably 1.5-fold to 5-fold more than that of the arbekacin free base solution. The precipitated carbamic acid derivative of arbekacin including arbekacin carbonate is preferably separated by a commonly-used method, for example, filtration, and then dried.

—In Case of Using any One of Carbonate and Hydrogen Carbonate—

In the case where any one of a carbonate and a hydrogen carbonate is added to the solution containing arbekacin free base in the step (a), a solvent to be used should be such that the arbekacin free base and the carbonate can be completely dissolved therein. It is possible to use water, or a solvent mixture of water with methanol, ethanol, propanol, dimethyl sulfoxide, acetonitrile, pyridine, tetrahydrofuran, acetone, or N,N-dimethylformamide. Water is preferable. The amount of the solvent used is not particularly limited, as long as the amount allows the dissolution of the raw materials arbekacin free base and carbonate. Nevertheless, the amount is preferably 1.6-fold to 200-fold more than that of the arbekacin free base. When the carbonate is added to the solution containing arbekacin free base, the temperature is not particularly limited, and the addition can be carried out at any temperature. The temperature is preferably 0 to 30° C. As the carbonate used when the carbonate is added to the solution containing arbekacin free base to form the carbamic acid derivative of arbekacin including arbekacin carbonate, it is possible to use: a metal salt or ammonium salt of a carbonate ion such as sodium carbonate, potassium carbonate, or ammonium carbonate; or a metal salt or ammonium salt of a hydrogen carbonate ion such as sodium hydrogen carbonate or ammonium hydrogen carbonate. Ammonium carbonate or ammonium hydrogen carbonate is preferable. A preferable amount of the carbonate used is 0.5 mol (i.e., 0.5 equivalents) or more, more preferably 0.5 mol to 3.0 mol, relative to 1 mol of the arbekacin free base. Particularly preferably, ammonium carbonate or ammonium hydrogen carbonate is added in an amount of 0.5 to 3.0 mol relative to 1 mol of the arbekacin free base. This makes it possible to prepare a solution containing arbekacin derivatives including arbekacin carbonate represented by the formula (1) and carbamic acid of arbekacin represented by the formula (2) (i.e., carbamic acid derivative of arbekacin including arbekacin carbonate). Note that in the case where the carbonate is added to the solution containing arbekacin free base as described above, arbekacin carbonate containing a carbonate ion represented by $CO_3^{2-}$ is obtained as the arbekacin carbonate. Meanwhile, in the case where the hydrogen carbonate is added, arbekacin carbonate containing a hydrogen carbonate ion represented by $HCO_3^-$ (i.e., arbekacin hydrogen carbonate) is obtained as the arbekacin carbonate.

In the case where the solvent used in the step (a) is a mixture solution of water with an organic solvent, the addition of any one of a carbonate and a hydrogen carbonate can precipitate the carbamic acid derivative of arbekacin including arbekacin carbonate in the solution without further adding any organic solvent (i.e., can form a slurry solution). In this case, the step (a) and the step (b) constitute one inseparable step.

On the other hand, in the case where water is used as the solvent in the step (a), even when any one of a carbonate and a hydrogen carbonate is added, the carbamic acid derivative of arbekacin including arbekacin carbonate does not precipitate in the solution. For this reason, in the step (b), the solution prepared in the step (a) is mixed with an organic solvent, thereby precipitating the carbamic acid derivative of arbekacin including arbekacin carbonate. In this case, the organic solvent to be used is not particularly limited, as long as the solvent allows the precipitation of the carbamic acid derivative of arbekacin including arbekacin carbonate. Nevertheless, the organic solvent is preferably one or a solvent mixture selected from the group consisting of methanol, ethanol, propanol, dimethyl sulfoxide, acetonitrile, pyridine, tetrahydrofuran, acetone, and N,N-dimethylformamide. Methanol or ethanol is further preferable. The amount of the solvent used is not particularly limited, as long as the amount allows the precipitation of the carbamic acid derivative of arbekacin including arbekacin carbonate. The precipitated carbamic acid derivative of arbekacin including arbekacin carbonate is preferably separated by a commonly-used method, for example, filtration, and then dried.

—Further Purification—

The separated carbamic acid derivative of arbekacin including arbekacin carbonate can also be further purified by repeating any purification method known to those skilled in the art (for example, a method in which the isolated carbamic acid derivative of arbekacin including arbekacin carbonate is dissolved in an appropriate solvent, then precipitated by cooling or adding an organic solvent, and separated by, for example, filtration; a method in which a solvent is added to the isolated carbamic acid derivative of arbekacin including arbekacin carbonate and stirred; or other methods).

<Production Method for Arbekacin Free Base>

Arbekacin free base produced by any method known to those skilled in the art normally contains approximately 1 to 2% of related substances. On the other hand, in a case where arbekacin free base is produced according to the present invention by producing a carbamic acid derivative of arbekacin including arbekacin carbonate from arbekacin free base, purifying the product by any purification method known to those skilled in the art if necessary, and removing carbon dioxide from the purified product, the arbekacin free base has a related substance content decreased to 0.5% or less.

Thus, the present invention provides a production method for arbekacin free base having a related substance content of 0.5% or less, the production method comprising a step of removing carbon dioxide from the carbamic acid derivative of arbekacin including arbekacin carbonate produced by the above-described method.

Such a production method for arbekacin free base includes chromatography. As a support used in the chromatography, it is possible to use a cation exchange resin, an anion exchange resin, or a porous resin. The amount of the support used is not particularly limited, as long as the amount allows the removal of carbon dioxide (i.e., allows decarboxylation) while arbekacin of the carbamic acid derivative of arbekacin including arbekacin carbonate is being held, or the amount allows washing off of the arbekacin free base while carbon dioxide (carbonate ion) of the carbamic acid derivative of arbekacin including arbekacin carbonate is being held. As a solvent used in the chromatography, it is possible to use generally-used solvents for cation exchange resins, anion exchange resins, and porous resins. The solvent is preferably water or ammonia water for a cation exchange resin; water for an anion exchange resin; and one or a solvent mixture selected from the group consisting of water, methanol, ethanol, and propanol for a porous resin. The resulting arbekacin free base is isolated by concentration to dryness, spray-drying, freeze-drying, or the like.

<Production Method for Pharmaceutically Acceptable Salt of Arbekacin>

A pharmaceutically acceptable salt of arbekacin produced by any method known to those skilled in the art normally contains approximately 1 to 2% of related substances. On the other hand, in a case where a pharmaceutically acceptable salt of arbekacin is produced according to the present invention by producing a carbamic acid derivative of arbekacin including arbekacin carbonate from arbekacin free base, purifying the product by any purification method known to those skilled in the art if necessary, and adding an acid to the purified product, the pharmaceutically acceptable salt has a related substance content decreased to 0.5% or less.

Thus, the present invention provides a production method for a pharmaceutically acceptable salt of arbekacin, the production method comprising a step of adding an acid to the carbamic acid derivative of arbekacin including arbekacin carbonate produced by the above-described method, the pharmaceutically acceptable salt having a related substance content of 0.5% or less, and represented by the following formula (3):

[Chem. 8]

Formula (3)

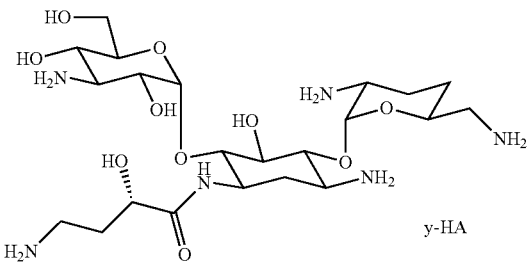

y-HA

[in the formula, y represents 1 to 5, and HA represents a pharmaceutically acceptable acid].

In this method, the carbamic acid derivative of arbekacin including arbekacin carbonate may be dispersed in a solvent or dissolved in a solvent for use. The solvent for the dispersion or dissolution is one or a solvent mixture selected from the group consisting of water, methanol, ethanol, propanol, dimethyl sulfoxide, acetonitrile, pyridine, tetrahydrofuran, acetone, and N,N-dimethylformamide. The amount of the solvent used is not particularly limited, as long as the amount allows the dissolution or the dispersion of the carbamic acid derivative of arbekacin including arbekacin carbonate. Any acid is usable without particular limitation, as long as it is capable of forming a pharmaceutically acceptable salt (acid salt) of arbekacin. Herein, the phrase "pharmaceutically acceptable" means that a compound or a combination of compounds is compatible with the other ingredients of a formulation and not harmful to a patient or a subject receiving it. Acids usable for forming a pharmaceutically acceptable acid salt of arbekacin include inorganic acids such as hydrochloric acid, hydrobromic acid, sulfuric acid, and phosphoric acid; and organic acids such as oxalic acid, maleic acid, succinic acid, citric acid, and sulfonic acids, but are not limited thereto. The resulting pharmaceutically acceptable salt of arbekacin can be isolated by concentration to dryness, spray-drying, freeze-drying, or the like. When a pharmaceutically acceptable salt of arbekacin is produced by adding an acid to the carbamic acid derivative of arbekacin including arbekacin carbonate and the salt is precipitated, the salt is separated by a commonly-used method, for example, filtration, and then dried, so that solids thereof can be obtained. Note that the term "pharmaceutically acceptable salt of arbekacin" is also meant to include a hydrate and a solvate of the salt. An example of the solvate includes an ethanolate.

Preferable Embodiments of the Present Invention

A preferable embodiment of the present invention includes

[13] a production method for a carbamic acid derivative of arbekacin represented by the following formula (2):

[Chem. 10]

Formula (2)

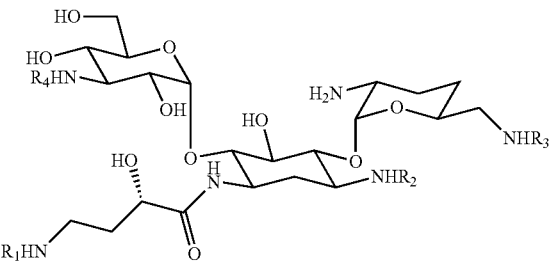

[in the formula, at least one of $R_1$, $R_2$, $R_3$, and $R_4$ is COOH, while the rest represent H] and including arbekacin carbonate represented by the following formula (1):

[Chem. 9]

Formula (1)

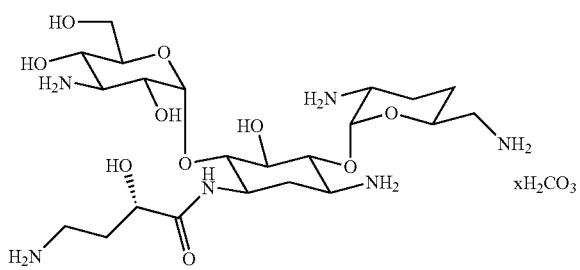

[in the formula, x represents 1 to 5], the production method comprising:

(a) a step of adding carbon dioxide to a solution in which arbekacin free base is dissolved in water whose amount is 1.6-fold to 200-fold more than that of the arbekacin free base, thereby preparing a solution having a pH of 7.5 to 9.0 and containing a carbamic acid derivative of arbekacin including arbekacin carbonate, or adding any one of ammonium carbonate and ammonium hydrogen carbonate in an amount of 0.5 to 3.0 equivalents to the solution in which arbekacin free base is dissolved in water whose amount is 1.6-fold to 200-fold more than that of the arbekacin free base, thereby preparing a solution containing a carbamic acid derivative of arbekacin including arbekacin carbonate;

(b) a step of mixing the prepared solution with any one of methanol and ethanol whose amount is 1.5- to 5-fold more than that of the solution, thereby precipitating the carbamic acid derivative of arbekacin including arbekacin carbonate in the solution; and (c) a step of separating the precipitated carbamic acid derivative of arbekacin including arbekacin carbonate.

A more preferable embodiment includes

[14] the production method according to [13], comprising:

(a) a step of adding carbon dioxide to the solution in which arbekacin free base is dissolved in water whose amount is 1.6-fold to 200-fold more than that of the arbekacin free base, thereby preparing the solution having a pH of 7.5 to 9.0 and containing the carbamic acid derivative of arbekacin including arbekacin carbonate;

(b) the step of mixing the prepared solution with any one of methanol and ethanol whose amount is 1.5- to 5-fold more than that of the solution, thereby precipitating the carbamic acid derivative of arbekacin including arbekacin carbonate in the solution; and (c) the step of separating the precipitated carbamic acid derivative of arbekacin including arbekacin carbonate.

A particularly preferable embodiment includes

[15] the production method according to [13], comprising:

(a) a step of adding carbon dioxide to a solution in which arbekacin free base is dissolved in water whose amount is 5-fold more than that of the arbekacin free base, thereby preparing the solution having a pH of 7.5 to 9.0 and containing the carbamic acid derivative of arbekacin including arbekacin carbonate;

(b) a step of mixing the prepared solution with ethanol whose amount is 2-fold more than that of the solution, thereby precipitating the carbamic acid derivative of arbekacin including arbekacin carbonate in the solution; and (c) a step of separating the precipitated carbamic acid derivative of arbekacin including arbekacin carbonate.

Another particularly preferable embodiment includes

[16] the production method according to [13], comprising:

(a) a step of adding any one of ammonium carbonate and ammonium hydrogen carbonate in an amount of 0.5 to 3.0 equivalents to a solution in which arbekacin free base is dissolved in water whose amount is 5-fold more than that of the arbekacin free base, thereby preparing the solution containing the carbamic acid derivative of arbekacin including arbekacin carbonate;

(b) a step of mixing the prepared solution with ethanol whose amount is 2-fold more than that of the solution, thereby precipitating the carbamic acid derivative of arbekacin including arbekacin carbonate in the solution; and (c) the step of separating the precipitated carbamic acid derivative of arbekacin including arbekacin carbonate.

Another preferable embodiment includes

[17] a production method for arbekacin free base having a related substance content of 0.5% or less, the production method comprising:

if necessary, purifying by any purification method known to those skilled in the art the carbamic acid derivative of arbekacin including arbekacin carbonate obtained by the method according to any one of [13] to [16]; and removing carbon dioxide therefrom using a cation exchange resin.

Still another preferable embodiment includes

[18] a production method for arbekacin sulfate having a related substance content of 0.5% or less, the production method comprising:

if necessary, purifying by any purification method known to those skilled in the art the carbamic acid derivative of arbekacin including arbekacin carbonate obtained by the method according to any one of [13] to [16]; and adding dilute sulfuric acid thereto.

EXAMPLES

Hereinafter, the present invention will be more specifically described based on Examples. However, the present invention is not limited to the following Examples.

[Raw Material]

As a raw material of the present invention, arbekacin free base is used. It is possible to use arbekacin free base produced by any method known to those skilled in the art, for example, the method described in Journal of Synthetic Organic Chemistry, Japan, 57 (5), 368-373 (1999), or a method in which sulfuric acid is removed from commercially-available arbekacin sulfate by a column chromatographic method using an ion exchange resin.

[Structure Analysis by NMR]

Figure 2:
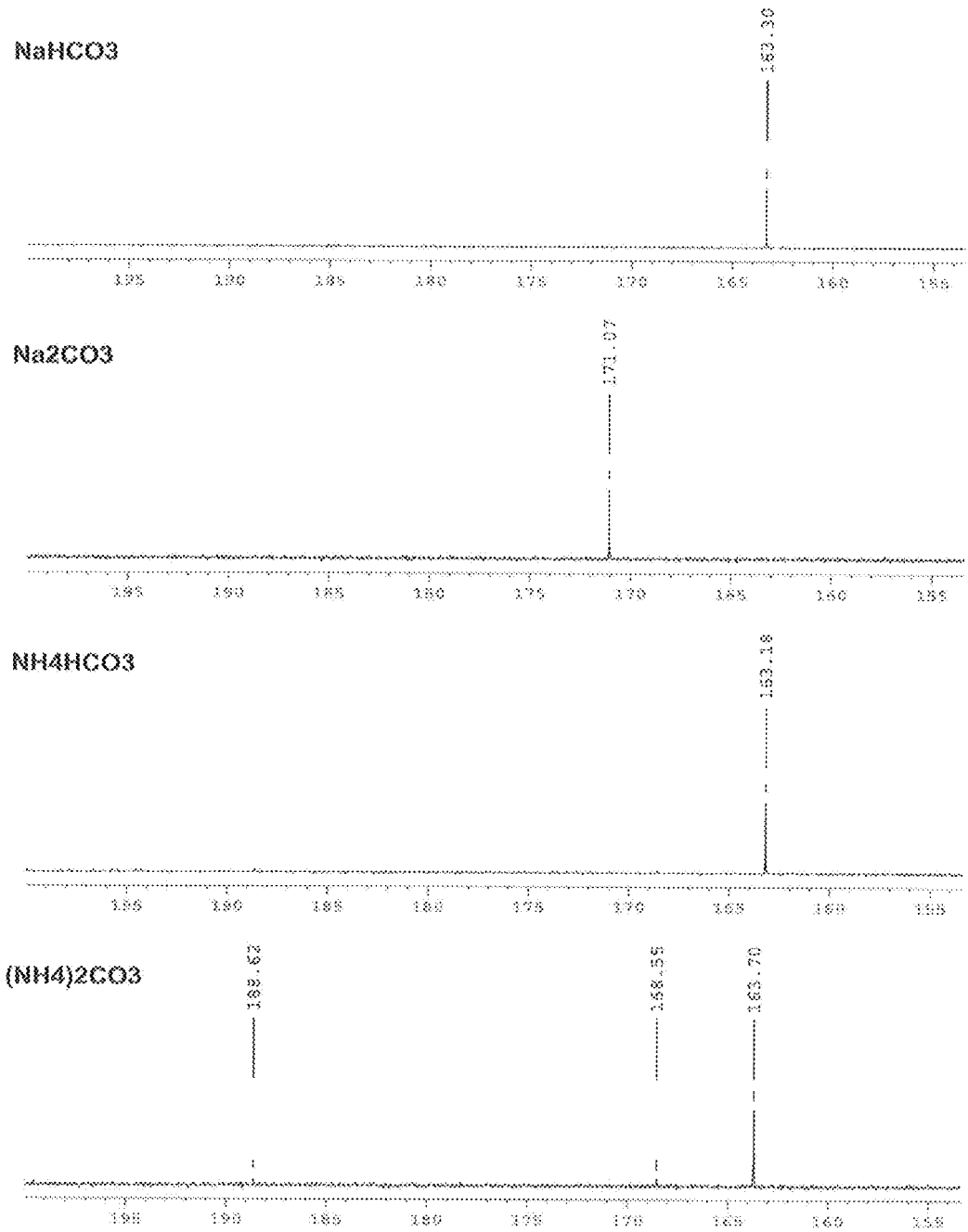
FIG. 2 is a figure showing the measurement result of 13C-NMR spectra of sodium hydrogen carbonate, sodium carbonate, ammonium hydrogen carbonate, and ammonium carbonate.

From the 13C-NMR measurement result of aqueous solutions of sodium hydrogen carbonate ($NaHCO_3$) and sodium carbonate ($Na_2CO_3$), the present inventors confirmed that the carbon signal of a hydrogen carbonate (salt containing a hydrogen carbonate ion represented by $HCO_3^-$) was around 163 ppm, and that the carbon signal of a carbonate (salt containing a carbonate ion represented by $CO_3^{2-}$) was around 171 ppm (FIG. 2). Moreover, from the 13C-NMR measurement result of an aqueous solution of ammonium hydrogen carbonate ($NH_4HCO_3$) and ammonium carbonate (($NH_4)_2CO_3$, mixture of ammonium hydrogen carbonate with carbamic acid ammonium salt), the carbon signal of carbamic acid was thought around 169 ppm (FIG. 2).

Next, sodium carbonate in an amount of 15 equivalents was added to an aqueous solution of arbekacin free base to observe signals newly generated by 13C-NMR. As a result, the observation showed that multiple signals were generated at 170.87 ppm and at 166.73 to 167.13 ppm, which were respectively thought of carbon of a carbonate (arbekacin carbonate containing a carbonate ion represented by $CO_3^{2-}$) and carbon of carbamic acid (carbamic acid of arbekacin) (top of FIG. 3).

[Chem. 11]

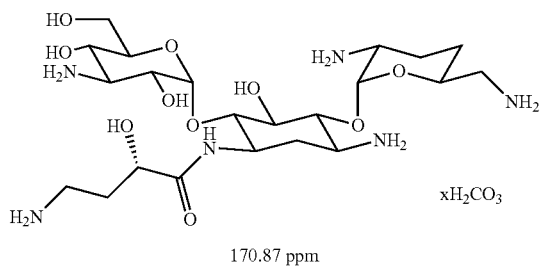

170.87 ppm

[Chem. 12]

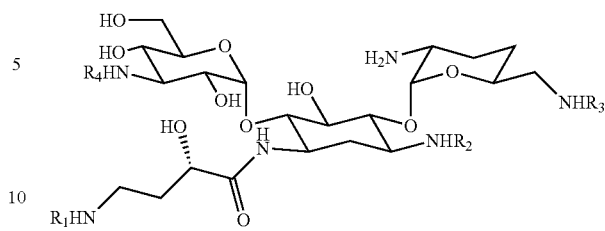

Any one or more of $R_1$, $R_2$, $R_3$, and $R_4$ are COOH 166.73~167.13 ppm

Figure 3:
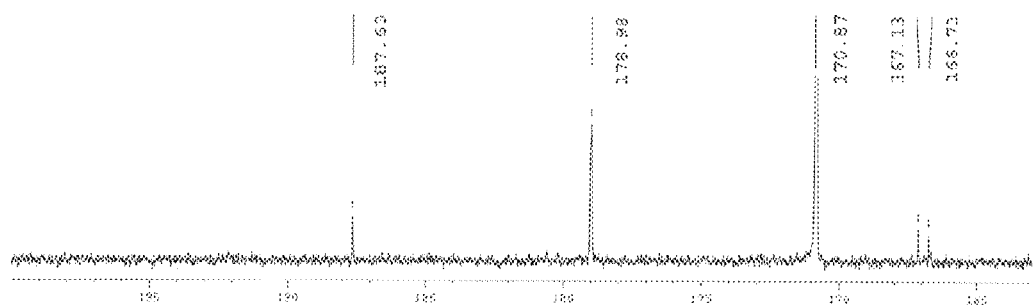
FIG. 3 is a figure showing the measurement result of 13C-NMR spectra of arbekacin free base+sodium carbonate.
Figure 3:
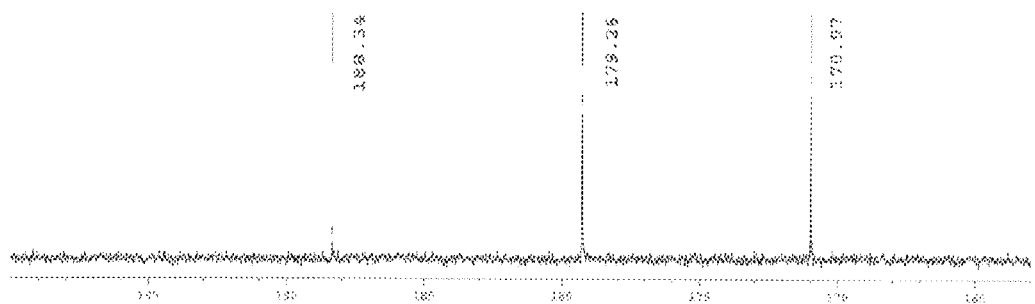
Figure 3:
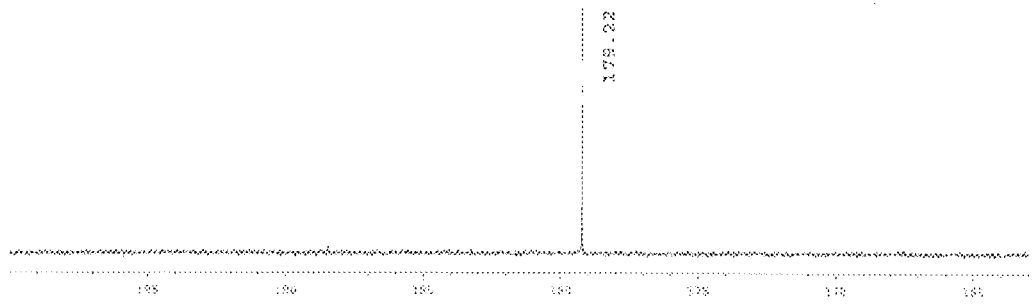
Figure 4:
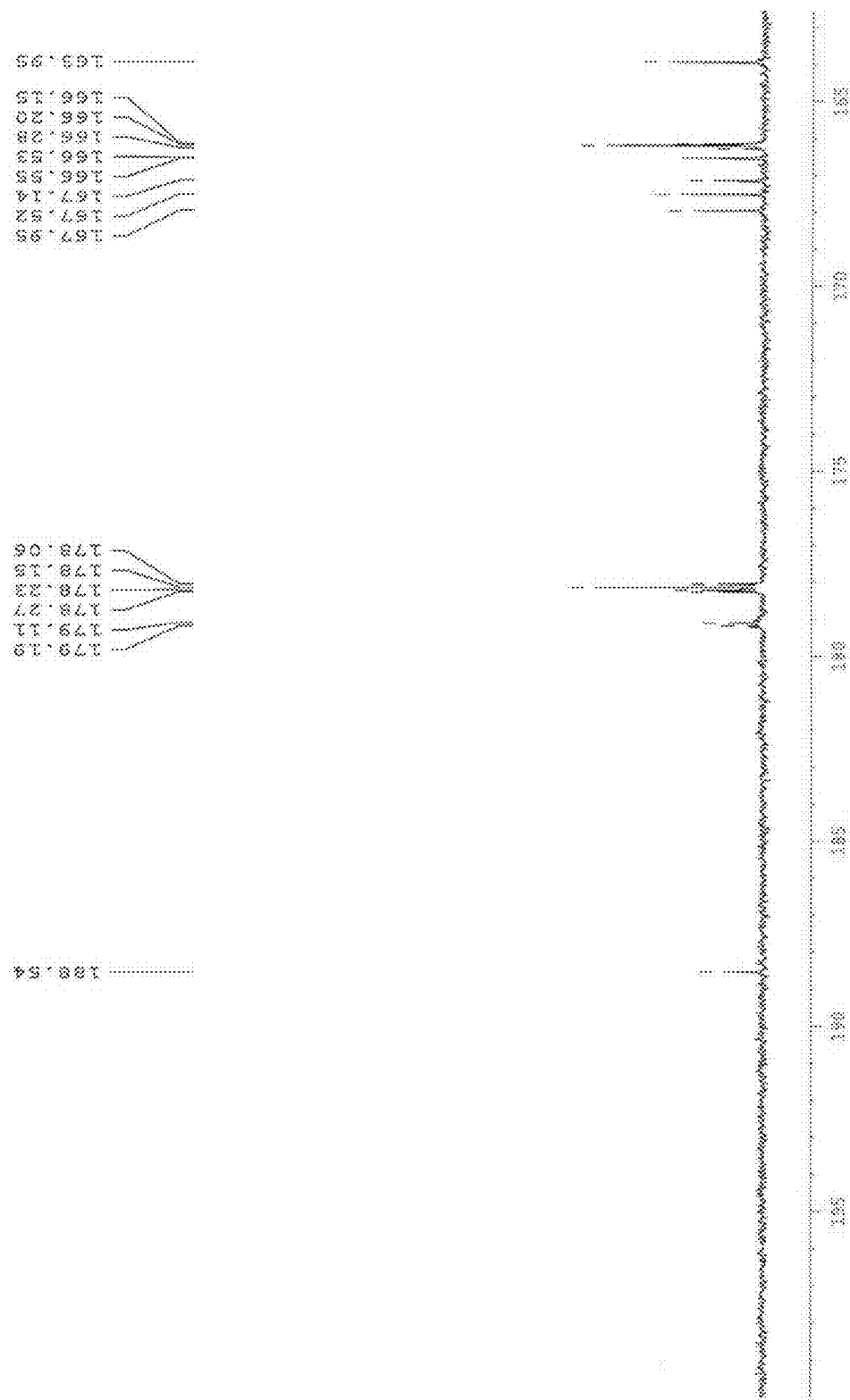
FIG. 4 is a figure showing the measurement result of a 13C-NMR spectrum of arbekacin free base+carbon dioxide.

Nevertheless, in the case where sodium carbonate was added to the aqueous solution of arbekacin free base, sodium carbonate had to be in an amount exceeding 3 equivalents relative to the arbekacin free base in order to generate sufficient signals thought of carbamic acid (FIG. 3). Hence, the condition for efficiently forming carbamic acid was earnestly studied. As a result, a method for adding carbon dioxide to an aqueous solution of arbekacin free base was found. Further, it was found that adding ethanol to this aqueous solution precipitated solids. As a result of the 13C-NMR analysis on the solids obtained in this manner, multiple signals were observed at 163.95 ppm and at 166.15 to 167.95 ppm, which were respectively thought of a hydrogen carbonate (arbekacin hydrogen carbonate containing a hydrogen carbonate ion represented by $HCO_3^-$) and carbamic acid (carbamic acid of arbekacin) (FIG. 4). This result suggested that adding carbon dioxide to an aqueous solution of arbekacin free base simultaneously formed carbamic acid of arbekacin and arbekacin carbonate (arbekacin carbonate containing a hydrogen carbonate ion represented by $HCO_3^-$ (i.e., arbekacin hydrogen carbonate)).

Figure 5:
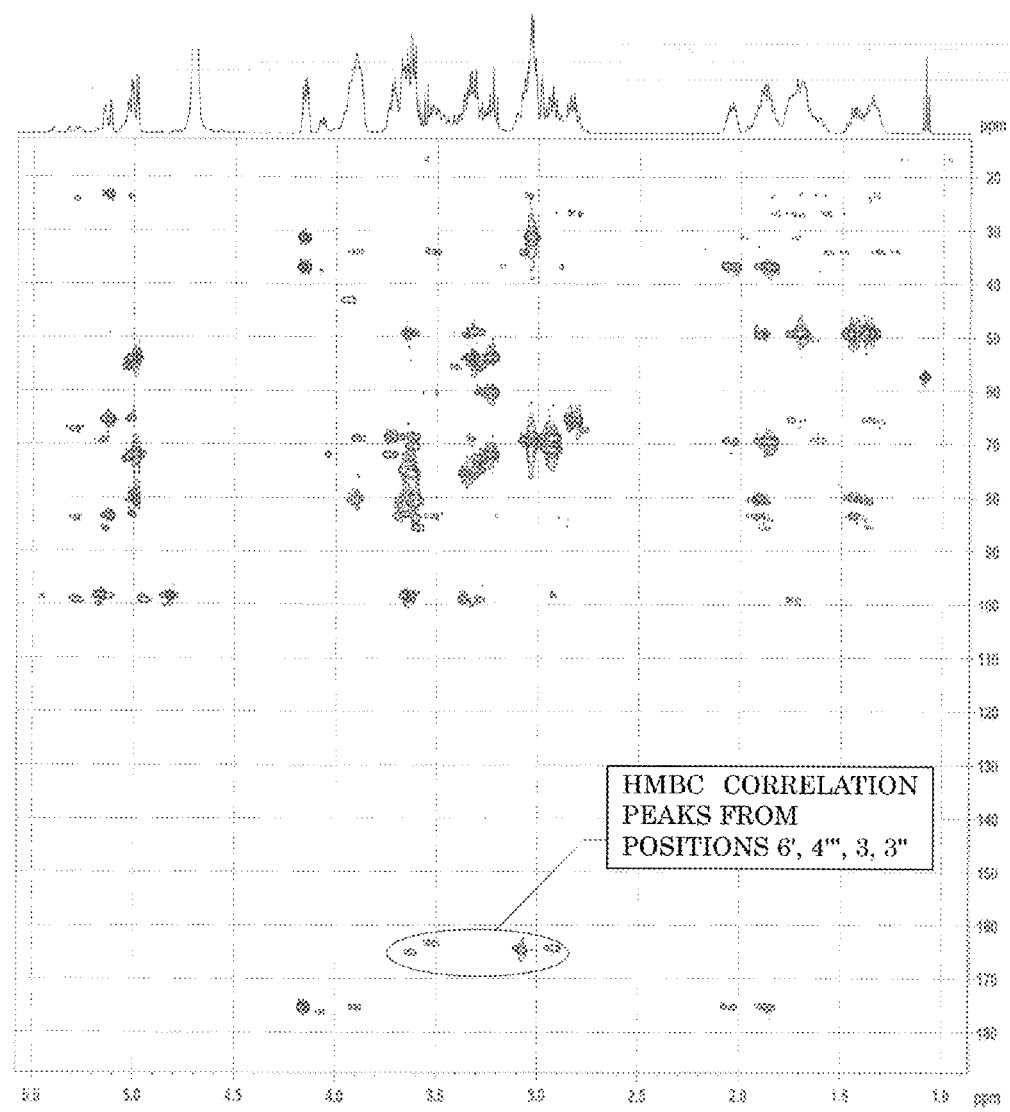
FIG. 5 is a figure showing the measurement result of an HMBC spectrum of arbekacin free base+carbon dioxide.

Furthermore, the solids obtained in the above-described manner were measured by two-dimensional NMR (HMBC (Heteronuclear Multiple Bond Correlation spectroscopy) method for observing correlations between 1H and 13C separated with 2 or 3 bonds (see the following equation)). As a result, HMBC correlation peaks from positions 6', 4''', 3, and 3' of arbekacin were observed around 166 ppm (FIG. 5). This result revealed that arbekacin and carbon dioxide were bonded to each other through formation of carbamic acid. The above results revealed that adding any one of carbon dioxide, a carbonate, and a hydrogen carbonate to a solution of arbekacin free base formed arbekacin derivatives including arbekacin carbonate and carbamic acid of arbekacin (i.e., carbamic acid derivative of arbekacin including arbekacin carbonate).

[Chem. 13]

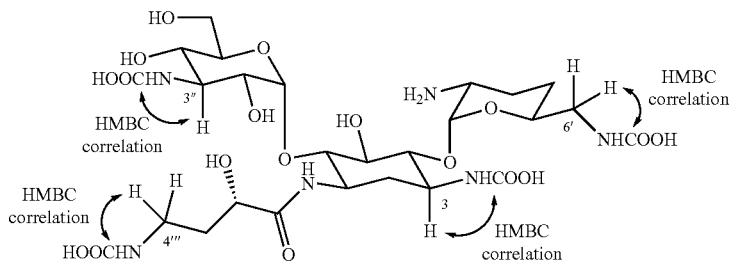

Subsequently, a carbamic acid derivative of arbekacin including arbekacin carbonate (arbekacin carbonate containing a hydrogen carbonate ion represented by $HCO_3^-$ (i.e., arbekacin hydrogen carbonate)) was isolated at different pH levels when carbon dioxide was added to an aqueous solution of arbekacin free base, and the 13C-NMR analysis was conducted. The following Tables 1 and 2 show the result of conducting the 13C-NMR measurement on carbamic acid derivatives of arbekacin including arbekacin carbonate obtained in Examples 2 and 3 below. In the comparison between the result from the solution pH of 6.1 (Example 2) and the result from the pH of 10.5 (Example 3) when carbon dioxide was added, the number of signals greatly differed; besides, the number of signals thought of carbonyl carbon at position 1''' around 177 to 179 ppm differed, and the chemical shifts of the other signals differed. These revealed that mixtures in multiple states were formed which were different in the position and the number of carbamic acids formed as well as the number of carbonates.

Further, the present inventors earnestly studied the condition for efficiently forming carbamic acid other than the use of carbon dioxide. As a result, it was found that methods for adding ammonium carbonate or ammonium hydrogen carbonate to an aqueous solution of arbekacin free base efficiently formed a carbamic acid derivative of arbekacin including arbekacin carbonate (arbekacin carbonate containing a carbonate ion represented by $CO_3^{2-}$, or arbekacin hydrogen carbonate containing a hydrogen carbonate ion represented by $HCO_3^-$). In this case also, the 13C-NMR measurement result revealed that mixtures in multiple states were formed which were different in the position and the number of carbamic acids formed as well as the number of carbonates, depending the amount of the carbonate added. The following Tables 1 and 2 show the result of conducting the 13C-NMR measurement on carbamic acid derivatives of arbekacin including arbekacin carbonate obtained in Examples 6 and 7 below. Note that, the following formula shows the positions of groups of arbekacin free base.

[Chem. 14]

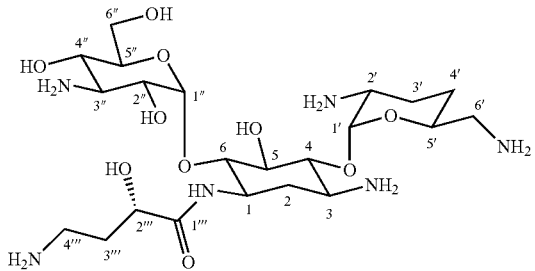

TABLE 1

| arbekacin free base | free base + carbon dioxide | | free base + ammonium carbonate | |
|---|---|---|---|---|
| (assignment of each signal) | Example 2 (pH 6.1) | Example 3 (pH 10.5) | Example 6 (3 eq.) | Example 7 (0.5 eq.) |
| 179.2 (1''') | 179.01 | 179.06 | 178.99 | 179.08 |
| 103.9 (1') | 178.11 | 178.74 | 178.08 | 178.98 |
| 101.1 (1'') | 178.01 | 167.37 | 177.94 | 178.32 |
| 89 (4) | 167.84 | 166.98 | 177.87 | 178.26 |

TABLE 1-continued

| arbekacin free base | free base + carbon dioxide | | free base + ammonium carbonate | |
|---|---|---|---|---|
| (assignment of each signal) | Example 2 (pH 6.1) | Example 3 (pH 10.5) | Example 6 (3 eq.) | Example 7 (0.5 eq.) |
| 83.3 (6) | 167.41 | 166.08 | 167.82 | 178.18 |
| 77.9 (5) | 167.03 | 103.90 | 167.39 | 178.10 |
| 74.8 (5'') | 166.41 | 103.37 | 167.03 | 167.83 |
| 74.4 (2'') | 166.08 | 101.02 | 166.40 | 167.40 |
| 73.4 (5') | 163.84 | 100.80 | 166.05 | 167.01 |
| 72.7 (2''') | 102.64 | 89.33 | 163.49 | 166.43 |
| 72.1 (4'') | 101.60 | 88.42 | 102.63 | 166.09 |
| 63.1 (6'') | 101.36 | 85.48 | 101.36 | 165.07 |
| 56.9 (3'') | 101.28 | 83.16 | 101.12 | 103.06 |
| 52.7 (2') | 101.16 | 82.96 | 101.01 | 102.80 |
| 52.4 (1) | 101.05 | 82.74 | 100.94 | 102.67 |
| 51.9 (3) | 100.90 | 78.49 | 100.80 | 102.55 |
| 47.8 (6') | 100.64 | 77.76 | 100.69 | 102.35 |
| 40.1 (4''') | 100.55 | 77.69 | 100.58 | 102.14 |
| 38.5 (3''') | 88.44 | 74.64 | 100.40 | 101.44 |
| 37.2 (2) | 86.24 | 74.23 | 100.09 | 101.12 |
| 30.3 (4') | 86.13 | 72.67 | 86.23 | 101.02 |
| 28.7 (3') | 85.87 | 72.42 | 86.15 | 100.89 |
| | 83.39 | 72.03 | 85.88 | 89.02 |
| | 82.94 | 71.82 | 83.45 | 87.45 |
| | 82.16 | 69.80 | 83.03 | 87.20 |
| | 78.31 | 62.90 | 82.19 | 86.12 |
| | 77.98 | 60.06 | 78.87 | 83.33 |
| | 77.71 | 56.67 | 78.25 | 83.28 |
| | 75.54 | 53.47 | 77.99 | 83.08 |
| | 74.82 | 52.46 | 77.68 | 82.84 |
| | 74.73 | 52.25 | 75.57 | 78.40 |
| | 73.91 | 51.92 | 74.85 | 77.89 |

TABLE 2

Chemical shift (ppm) (continued from Table 1)

| arbekacin free base | free base + carbon dioxide | | free base + ammonium carbonate | |
|---|---|---|---|---|
| (assignment of each signal) | Example 2 (pH 6.1) | Example 3 (pH 10.5) | Example 6 (3 eq.) | Example 7 (0.5 eq.) |
| | 73.61 | 51.78 | 74.70 | 77.71 |
| | 73.25 | 48.12 | 73.66 | 77.58 |
| | 72.35 | 47.41 | 73.23 | 74.70 |
| | 72.14 | 46.60 | 72.33 | 74.16 |
| | 72.05 | 40.20 | 72.16 | 74.01 |
| | 71.66 | 39.81 | 72.06 | 73.30 |
| | 71.58 | 36.94 | 71.44 | 72.38 |
| | 71.45 | 36.78 | 71.33 | 72.08 |
| | 69.71 | 30.04 | 71.14 | 71.86 |
| | 68.21 | 28.35 | 71.06 | 71.79 |
| | 68.03 | 27.95 | 69.15 | 71.45 |
| | 63.26 | 19.47 | 68.11 | 71.22 |
| | 63.04 | 1.17 | 67.95 | 70.99 |
| | 62.92 | | 63.29 | 70.88 |
| | 60.11 | | 63.03 | 68.59 |
| | 58.39 | | 62.85 | 62.93 |
| | 56.79 | | 58.35 | 60.09 |
| | 56.71 | | 56.77 | 58.46 |
| | 53.23 | | 53.22 | 56.71 |
| | 53.12 | | 52.70 | 53.30 |
| | 52.72 | | 52.38 | 52.71 |
| | 52.43 | | 52.12 | 52.48 |
| | 52.16 | | 52.01 | 52.27 |
| | 52.07 | | 51.95 | 52.20 |
| | 51.85 | | 51.81 | 52.14 |
| | 51.72 | | 51.66 | 51.90 |
| | 47.94 | | 47.85 | 51.76 |
| | 46.27 | | 45.96 | 48.06 |
| | 45.99 | | 45.68 | 46.86 |
| | 45.79 | | 40.25 | 46.67 |

TABLE 2-continued

Chemical shift (ppm) (continued from Table 1)

| arbekacin free base | free base + carbon dioxide | | free base + ammonium carbonate | |
|---|---|---|---|---|
| (assignment of each signal) | Example 2 (pH 6.1) | Example 3 (pH 10.5) | Example 6 (3 eq.) | Example 7 (0.5 eq.) |
| | 40.26 | | 39.60 | 46.06 |
| | 39.63 | | 37.15 | 40.20 |
| | 37.18 | | 36.99 | 39.68 |
| | 36.86 | | 36.81 | 37.19 |
| | 33.93 | | 36.73 | 36.90 |
| | 33.74 | | 33.72 | 34.93 |
| | 30.25 | | 33.61 | 34.84 |
| | 29.81 | | 30.23 | 34.79 |
| | 29.54 | | 29.34 | 29.89 |
| | 26.61 | | 26.56 | 29.79 |
| | 26.49 | | 25.26 | 27.68 |
| | 26.31 | | 24.98 | 27.56 |
| | 25.89 | | 1.19 | 27.12 |
| | 25.73 | | | 26.99 |
| | 25.54 | | | 26.55 |
| | 19.49 | | | 19.48 |

Example 1

After 1 g of arbekacin free base was dissolved in 5.5 mL of water, carbon dioxide was blown thereinto, and the pH was adjusted to 9.0. To this solution, 11 mL of ethanol was added and stirred, and a carbamic acid derivative of arbekacin including arbekacin carbonate was precipitated. The precipitated solid was isolated by filtration, washed with ethanol, and then dried. Thus, 0.95 g of arbekacin derivatives including arbekacin carbonate and carbamic acid of arbekacin (i.e., carbamic acid derivative of arbekacin including arbekacin carbonate) were obtained. In the HPLC analysis on the obtained carbamic acid derivative of arbekacin including arbekacin carbonate, the relative retention time (the retention time of the sample/the retention time of the standard substance) was 1.0, and the related substance content was 0.4%, in which the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

Example 2

After 1 g of arbekacin free base was dissolved in 200 mL of water, carbon dioxide was blown thereinto, and the pH was adjusted to 6.1. To this solution, 1000 mL of ethanol was added and stirred, and a carbamic acid derivative of arbekacin including arbekacin carbonate was precipitated. The precipitated solid was isolated by filtration, washed with ethanol, and then dried. Thus, 0.64 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.3%, in which the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

Example 3

After 1 g of arbekacin free base was dissolved in 1.6 mL of water, carbon dioxide was blown thereinto, and the pH was adjusted to 10.5. To this solution, 20 mL of ethanol was added and stirred, and a carbamic acid derivative of arbekacin including arbekacin carbonate was precipitated. The precipitated solid was isolated by filtration, washed with ethanol, and then dried. Thus, 0.91 g of the carbamic acid derivative of arbekacin including arbekacin carbonate was obtained. In the HPLC analysis on the carbamic acid derivative of arbekacin including arbekacin carbonate, the relative retention time (the retention time of the sample/the retention time of the standard substance) was 1.0, and the related substance content was 1.2%, in which the dibekacin content was 0.5%. Note that, in this case, the arbekacin carbonate was arbekacin carbonate containing a hydrogen carbonate ion represented by $HCO_3^-$ (i.e., arbekacin hydrogen carbonate).

Example 4

After 1 g of arbekacin free base was dissolved in 2.4 mL of water, carbon dioxide was blown thereinto, and the pH was adjusted to 8.9. This solution was added to 8 mL of ethanol and stirred, and a carbamic acid derivative of arbekacin including arbekacin carbonate was precipitated. The precipitated solid was isolated by filtration, washed with ethanol, and then dried. Thus, 1.00 g of the carbamic acid derivative of arbekacin including arbekacin carbonate was obtained. In the HPLC analysis on the carbamic acid derivative of arbekacin including arbekacin carbonate, the relative retention time (the retention time of the sample/the retention time of the standard substance) was 1.0, and the related substance content was 1.8%, in which the dibekacin content was 0.8%. Note that, in this case, the arbekacin carbonate was arbekacin carbonate containing a hydrogen carbonate ion represented by $HCO_3^-$ (i.e., arbekacin hydrogen carbonate).

Example 5

After 1 g of arbekacin free base was dissolved in 10 mL of water, carbon dioxide was blown thereinto, and the pH was adjusted to 8.0. To this solution, 25 mL of ethanol was added and stirred, and a carbamic acid derivative of arbekacin including arbekacin carbonate was precipitated. The precipitated solid was isolated by filtration, washed with ethanol, and then dried. Thus, 1.07 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/ the retention time of the standard substance) was 1.0, the related substance content was 0.8%, in which the dibekacin content was 0.4%. Note that, in this case, the arbekacin carbonate was arbekacin carbonate containing a hydrogen carbonate ion represented by $HCO_3^-$ (i.e., arbekacin hydrogen carbonate).

Example 6

In 10 mL of water, 1 g of arbekacin free base and 3 equivalents of ammonium carbonate were dissolved. To this solution, 25 mL of ethanol was added and stirred, and a carbamic acid derivative of arbekacin including arbekacin carbonate was precipitated. The precipitated solid was isolated by filtration, washed with ethanol, and then dried. Thus, 0.96 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.3%, in which the dibekacin content was 0.1%. Note that, in this case, the arbekacin carbonate was arbekacin carbonate containing a carbonate ion represented by $CO_3^{2-}$.

Example 7

In 1.6 mL of water, 1 g of arbekacin free base and 0.5 equivalents of ammonium carbonate were dissolved. To this solution, 8 mL of ethanol was added and stirred, and a carbamic acid derivative of arbekacin including arbekacin carbonate was precipitated. The precipitated solid was isolated by filtration, washed with ethanol, and then dried. Thus, 0.35 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.5%, in which the dibekacin content was 0.1%. Note that, in this case, the arbekacin carbonate was arbekacin carbonate containing a carbonate ion represented by $CO_3^{2-}$.

Example 8

In 200 mL of water, 1 g of arbekacin free base and 102 equivalents of ammonium carbonate were dissolved. To this solution, 1000 mL of ethanol was added and stirred, and a carbamic acid derivative of arbekacin including arbekacin carbonate was precipitated. The precipitated solid was isolated by filtration, washed with ethanol, and then dried. Thus, 1.04 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.6%, in which the dibekacin content was 0.2%. Note that, in this case, the arbekacin carbonate was arbekacin carbonate containing a carbonate ion represented by $CO_3^{2-}$.

Example 9

In 10 mL of water, 1 g of arbekacin free base and 3 equivalents of ammonium hydrogen carbonate were dissolved. To this solution, 25 mL of ethanol was added and stirred, and a carbamic acid derivative of arbekacin including arbekacin carbonate was precipitated. The precipitated solid was isolated by filtration, washed with ethanol, and then dried. Thus, 0.96 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.2%, in which the dibekacin content was 0.0%. Note that, in this case, the arbekacin carbonate was arbekacin carbonate containing a hydrogen carbonate ion represented by $HCO_3^-$ (i.e., arbekacin hydrogen carbonate).

Example 10

In 10 mL of water, 1 g of arbekacin free base and 3 equivalents of sodium hydrogen carbonate were dissolved. This solution was added to 25 mL of ethanol and stirred, and a carbamic acid derivative of arbekacin including arbekacin carbonate was precipitated. The precipitated solid was isolated by filtration, washed with ethanol, and then dried. Thus, 0.35 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.4%, in which the dibekacin content was 0.4%. Note that, in this case, the arbekacin carbonate was arbekacin carbonate containing a hydrogen carbonate ion represented by $HCO_3^-$ (i.e., arbekacin hydrogen carbonate).

Example 11

After 3.0 g of arbekacin free base was dissolved in 16.4 mL of water, carbon dioxide was blown thereinto, and the pH was adjusted to 8.9. To this solution, 34 mL of methanol was added and stirred, and a carbamic acid derivative of arbekacin including arbekacin carbonate was precipitated. The precipitated solid was isolated by filtration, washed with methanol, and then dried. Thus, 1.93 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.4%, in which the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

Example 12

After 2.0 g of arbekacin free base was dissolved in 5.5 mL of water, carbon dioxide was blown thereinto, and the pH was adjusted to 8.9. To this solution, 22.7 mL of 2-propanol was added and stirred, and a carbamic acid derivative of arbekacin including arbekacin carbonate was precipitated. The precipitated solid was isolated by filtration, washed with 2-propanol, and then dried. Thus, 1.90 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.3%, in which the dibekacin content was 0.4%. Note that, in this case, the arbekacin carbonate was arbekacin carbonate containing a hydrogen carbonate ion represented by $HCO_3^-$ (i.e., arbekacin hydrogen carbonate).

Example 13

After 3.0 g of arbekacin free base was dissolved in 16.4 mL of water, carbon dioxide was blown thereinto, and the pH was adjusted to 8.9. To this solution, 34 mL of dimethyl sulfoxide was added and stirred, and a carbamic acid derivative of arbekacin including arbekacin carbonate was precipitated. The precipitated solid was isolated by filtration, washed with dimethylsulfoxide, and then dried. Thus, 3.32 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.1%, in which the dibekacin content was 0.0%. Note that, in this case, the arbekacin carbonate was arbekacin carbonate containing a hydrogen carbonate ion represented by $HCO_3^-$ (i.e., arbekacin hydrogen carbonate).

Example 14

After 2.0 g of arbekacin free base was dissolved in 5.5 mL of water, carbon dioxide was blown thereinto, and the pH was adjusted to 8.9. To this solution, 91 mL of acetonitrile was added and stirred, and a carbamic acid derivative of arbekacin including arbekacin carbonate was precipitated. The precipitated solid was isolated by filtration, washed with acetonitrile, and then dried. Thus, 2.50 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.5%, in which the dibekacin content was 0.5%. Note that, in this case, the arbekacin carbonate was arbekacin carbonate containing a hydrogen carbonate ion represented by $HCO_3^-$ (i.e., arbekacin hydrogen carbonate).

Example 15

After 2.0 g of arbekacin free base was dissolved in 5.5 mL of water, carbon dioxide was blown thereinto, and the pH was adjusted to 8.9. To this solution, 91 mL of tetrahydrofuran was added and stirred, and a carbamic acid derivative of arbekacin including arbekacin carbonate was precipitated. The precipitated solid was isolated by filtration, washed with tetrahydrofuran, and then dried. Thus, 2.12 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.5%, in which the dibekacin content was 0.5%. Note that, in this case, the arbekacin carbonate was arbekacin carbonate containing a hydrogen carbonate ion represented by $HCO_3^-$ (i.e., arbekacin hydrogen carbonate).

Example 16

After 2.0 g of arbekacin free base was dissolved in 10.9 mL of water, carbon dioxide was blown thereinto, and the pH was adjusted to 8.9. To this solution, 34 mL of pyridine was added and stirred, and a carbamic acid derivative of arbekacin including arbekacin carbonate was precipitated. The precipitated solid was isolated by filtration, washed with pyridine, and then dried. Thus, 2.58 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.3%, in which the dibekacin content was 0.4%. Note that, in this case, the arbekacin carbonate was arbekacin carbonate containing a hydrogen carbonate ion represented by $HCO_3^-$ (i.e., arbekacin hydrogen carbonate).

Example 17

After 2.0 g of arbekacin free base was dissolved in 10.9 mL of water, carbon dioxide was blown thereinto, and the pH was adjusted to 8.9. To this solution, 22.7 mL of N,N-dimethylformamide was added and stirred, and a carbamic acid derivative of arbekacin including arbekacin carbonate was precipitated. The precipitated solid was isolated by filtration, washed with N,N-dimethylformamide, and then dried. Thus, 2.23 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 1.0%, in which the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

Example 18

In 10.9 mL of water, 2.0 g of arbekacin free base was dissolved, carbon dioxide was blown thereinto, and the pH was adjusted to 8.9. To this solution, 22.7 mL of acetone was added and stirred, and a carbamic acid derivative of arbekacin including arbekacin carbonate was precipitated. The precipitated solid was isolated by filtration, washed with acetone, and then dried. Thus, 2.13 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/ the retention time of the standard substance) was 1.0, and the related substance content was 0.9%, in which the dibekacin content was 0.3%. Note that, in this case, the arbekacin carbonate was arbekacin carbonate containing a hydrogen carbonate ion represented by $HCO_3^-$ (i.e., arbekacin hydrogen carbonate).

Example 19

In 16 mL of water, 3.0 g of arbekacin free base was dissolved, carbon dioxide was blown thereinto, and the pH was adjusted to 7.5. To this solution, 32 mL of ethanol was added and stirred, and a carbamic acid derivative of arbekacin including arbekacin carbonate was precipitated. The precipitated solid was isolated by filtration, washed with ethanol, and then dried. Thus, 3.40 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/ the retention time of the standard substance) was 1.0, the related substance content was 0.4%, and the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

Reference Example

In 20 mL of water, 5.0 g of arbekacin free base was dissolved, and the pH was adjusted to 7.0 using dilute sulfuric acid. This solution was subjected to freeze-drying. Thus, 7.17 g of arbekacin sulfate was obtained. In the HPLC analysis on the obtained arbekacin sulfate, the relative retention time (the retention time of the sample/the retention time of the standard substance) was 1.0, and the related substance content was 2.1%, in which the dibekacin content was 1.0%.

Example 20

(i) In 52 mL of water, 10.0 g of arbekacin free base in a lot used in Reference Example was dissolved, carbon dioxide was blown thereinto, and the pH was adjusted to 8.9. To this solution, 78 mL of ethanol was added and stirred, and a carbamic acid derivative of arbekacin including arbekacin carbonate was precipitated. The precipitated solid was isolated by filtration, washed with ethanol, and then dried. Thus, 10.73 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, and the related substance content was 0.4%, in which the dibekacin content was 0.1%. Note that, in this case, the arbekacin carbonate was arbekacin carbonate containing a hydrogen carbonate ion represented by $HCO_3^-$ (i.e., arbekacin hydrogen carbonate).

(ii) In 160 mL of water, 4.0 g of the carbamic acid derivative of arbekacin including arbekacin carbonate obtained in (i) was dissolved, and adsorbed to 50 mL of a weakly acidic cation exchange resin. The resin was washed with water and carbon dioxide was removed. Then, 1 mol/L of ammonia water was passed through the resin, and a solution containing the arbekacin free base was obtained. This solution was subjected to freeze-drying. Thus, 3.91 g of the arbekacin free base was obtained. In the HPLC analysis on the obtained arbekacin free base, the relative retention time (the retention time of the sample/the retention time of the standard substance) was 1.0, and the related substance content was 0.4%, in which the dibekacin content was 0.2%.

Example 21

In 14 mL of water, 4.0 g of the carbamic acid derivative of arbekacin including arbekacin carbonate obtained in (i) of Example 20 was dissolved, and the pH was adjusted to 7.0 using dilute sulfuric acid. This solution was subjected to freeze-drying. Thus, 4.45 g of arbekacin sulfate was obtained. In the HPLC analysis on the obtained arbekacin sulfate, the relative retention time (the retention time of the sample/the retention time of the standard substance) was 1.0, and the related substance content was 0.4%, in which the dibekacin content was 0.2%.

Example 22

In a mixture solution of 50 mL of methanol with 10 mL of water, 3.0 g of arbekacin free base was dissolved, carbon dioxide was blown thereinto for 60 minutes, and a carbamic acid derivative of arbekacin including arbekacin carbonate was precipitated. The precipitated solid was isolated by filtration, washed with methanol, and then dried. Thus, 3.30 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, the related substance content was 0.4%, and the dibekacin content was 0.2%. Note that, in this case, the arbekacin carbonate was arbekacin carbonate containing a hydrogen carbonate ion represented by $HCO_3^-$ (i.e., arbekacin hydrogen carbonate).

Example 23

To 1.0 g of the carbamic acid derivative of arbekacin including arbekacin carbonate obtained in Example 14, 6 mL of a mixture solution of ethanol/water=1/1 was added and stirred for the dissolution. To this solution, 4 mL of ethanol was added, and a solid was precipitated. It was isolated by filtration, washed with ethanol, and then dried. Thus, 0.75 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/the retention time of the standard substance) was 1.0, the related substance content was 0.3%, and the dibekacin content was 0.0%.

Example 24

To 1.0 g of the carbamic acid derivative of arbekacin including arbekacin carbonate obtained in Example 15, 10 mL of a mixture solution of ethanol/water=2/1 was added and stirred. A solid was isolated by filtration, washed with ethanol, and then dried. Thus, 0.88 g of the carbamic acid derivative of arbekacin including arbekacin carbonate was obtained. In the HPLC analysis on the obtained carbamic acid derivative of arbekacin including arbekacin carbonate, the relative retention time (the retention time of the sample/ the retention time of the standard substance) was 1.0, the related substance content was 0.2%, and the dibekacin content was 0.1%.

[HPLC Analysis]

The HPLC analysis conditions were as described in (3) Dibekacin and (4) Related substance in the purity test for arbekacin sulfate in the Japanese Pharmacopoeia Sixteen Edition.

As has been described so far, the carbamic acid derivative of arbekacin including arbekacin carbonate obtained according to the present invention were mixtures in multiple states which were different in the position and the number of carbamic acids formed as well as the number of carbonates, depending on the formation conditions. According to the HPLC analysis on these, carbon dioxide was readily lost, and the peak was detected only in the same retention time as that of arbekacin free base used as the raw material. Table 3 shows the result of the HPLC analysis on arbekacin free base used as the raw material in each Example, and on the above-described carbamic acid derivative of arbekacin including arbekacin carbonate (i.e., arbekacin derivatives) obtained according to the present invention. The result shown in Table 3 revealed that the related substances were decreased in comparison with the arbekacin free base used as the raw material. In other words, it was found out that the method of the present invention made it possible to readily remove related substance by converting arbekacin free base to a carbamic acid derivative of arbekacin including arbekacin carbonate and isolating the resultant in a solid form, without using a conventional method for purifying arbekacin free base by chromatography.

TABLE 3

| Example | Arbekacin free base used as raw material lot No. | Arbekacin free base used as raw material related substance content (dibekacin amount) (%) | Carbamic acid derivative of arbecacin including arbekacin carbonate related substance content (dibekacin amount) (%) |
|---|---|---|---|
| Example 1 | 3 | 1.7(0.5) | 0.4(0.1) |
| Example 2 | 2 | 2.2(1.0) | 0.3(0.1) |
| Example 3 | 2 | 2.2(1.0) | 1.2(0.5) |
| Example 4 | 2 | 2.2(1.0) | 1.8(0.8) |
| Example 5 | 2 | 2.2(1.0) | 0.8(0.4) |
| Example 6 | 1 | 1.7(0.5) | 0.3(0.1) |
| Example 7 | 2 | 2.2(1.0) | 0.5(0.1) |
| Example 8 | 2 | 2.2(1.0) | 0.6(0.2) |
| Example 9 | 1 | 1.7(0.5) | 0.2(0.0) |
| Example 10 | 2 | 2.2(1.0) | 1.4(0.4) |
| Example 11 | 3 | 1.7(0.5) | 0.4(0.1) |
| Example 12 | 4 | 1.6(0.5) | 1.3(0.4) |
| Example 13 | 4 | 1.6(0.5) | 0.1(0.0) |
| Example 14 | 4 | 1.6(0.5) | 1.5(0.5) |
| Example 15 | 4 | 1.6(0.5) | 1.4(0.4) |
| Example 16 | 4 | 1.6(0.5) | 1.3(0.4) |
| Example 17 | 4 | 1.6(0.5) | 1.0(0.1) |
| Example 18 | 4 | 1.6(0.5) | 0.9(0.3) |
| Example 19 | 5 | 1.6(0.5) | 0.4(0.1) |
| Example 20 | 2 | 2.2(1.0) | a)0.4(0.1), b)0.4(0.2) |
| Example 21 | 2 | 2.2(1.0) | 0.4(0.2) |
| Example 22 | 5 | 1.6(0.5) | 0.4(0.2) |
| Example 24 | (compound obtained in Example 14) | | 0.3(0.0) |
| Example 24 | (compound obtained in Example 15) | | 0.2(0.1) |
| Reference Example | 2 | 2.2(1.0) | 2.1(1.0) |

Further, it was revealed that the carbamic acid derivative of arbekacin including arbekacin carbonate in the solid form was more stable than arbekacin free base (Table 4).

TABLE 4

| | Amount of related substances increased (%) Upper row: dibekacin, Lower row: related substance content | |
|---|---|---|
| | 40° C., 75% RH, 1-month storage | 40° C., 75% RH, 2-month storage |
| Example 1 | 0.0 | 0.1 |
| | 0.0 | 0.1 |
| Example 2 | 0.1 | 0.2 |
| | 0.2 | 0.2 |
| Example 3 | 0.2 | 0.3 |
| | 0.2 | 0.3 |
| Example 4 | 0.1 | 0.2 |
| | 0.1 | 0.3 |
| Example 5 | 0.1 | 0.1 |
| | 0.1 | 0.1 |
| Example 6 | 0.0 | 0.1 |
| | 0.0 | 0.1 |
| Example 7 | 0.2 | 0.2 |
| | 0.2 | 0.3 |
| Example 8 | 0.0 | 0.0 |
| | 0.0 | 0.0 |
| Example 9 | 0.0 | 0.1 |
| | 0.0 | 0.1 |
| Example 10 | 0.0 | 0.0 |
| | 0.0 | 0.2 |
| arbekacin free base | 1.2 | 2.2 |
| | 1.7 | 4.3 |

Specifically, arbekacin free base was stored at 40° C. and a humidity of 75% for 1 month and 2 months, and the amount of related substances changed was analyzed by HPLC. As a result, the observation showed that the amount of the related substances changed (i.e., the amount increased) was 4% or more. In contrast, in the case of the carbamic acid derivative of arbekacin including arbekacin carbonate obtained according to the present invention and stored under the same conditions, the increase in the amount of the related substances changed was only 0.3% or less. It was revealed that the effect of these was retained, when the carbamic acid derivative of arbekacin including arbekacin carbonate was obtained within preferable conditions, even if the position and the number of carbamic acids as well as the number of carbonates were different.

Furthermore, it was revealed that the carbamic acid derivative of arbekacin including arbekacin carbonate had low moisture-absorbing properties in comparison with arbekacin free base. Table 5 shows the result of measuring the moisture-absorbing properties when arbekacin free base and the compound obtained in Example 19 of the present invention were each stored at 40° C. and a humidity of 12, 22, 30, 43, and 53%.

TABLE 5

| | Humidity 12% | Humidity 22% | Humidity 30% | Humidity 43% | Humidity 53% |
|---|---|---|---|---|---|
| Arbekacin free base | 1.60 | 4.62 | 6.25 | 7.54 | 9.14 |
| Example 19 | −0.52 | 0.06 | 0.59 | 0.90 | 2.63 |

The above revealed that it was possible to easily store the carbamic acid derivative of arbekacin including arbekacin carbonate as a raw material of a pharmaceutically acceptable salt of arbekacin.

INDUSTRIAL APPLICABILITY

The present invention provides the carbamic acid derivative of arbekacin including arbekacin carbonate, and makes it possible to produce arbekacin free base and a pharmaceutically acceptable salt thereof efficiently with a high purity. The present invention can greatly contribute to particularly the medical field.

The invention claimed is:

1. A production method for a carbamic acid derivative of arbekacin represented by the following formula (2):

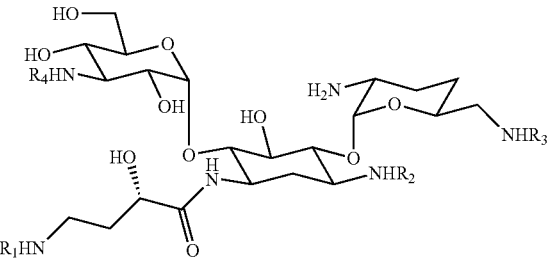

Formula (2)

in the formula, at least one of R1, R2, R3, and R4 is COOH, while the rest represent H and including arbekacin carbonate represented by the following formula (1):

Formula (1)

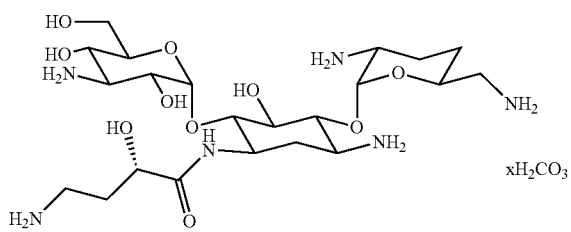

xH₂CO₃ in the formula, x represents 1 to 5, the production method comprising:
(a) a step of adding any one of carbon dioxide, a carbonate, and a hydrogen carbonate to a solution containing arbekacin free base, thereby preparing a solution containing a carbamic acid derivative of arbekacin including arbekacin carbonate;
(b) a step of precipitating the carbamic acid derivative of arbekacin including arbekacin carbonate in the solution; and
(c) a step of separating the precipitated carbamic acid derivative of arbekacin including arbekacin carbonate.

2. The production method according to claim 1, wherein, in the step (a), carbon dioxide is added to the solution containing arbekacin free base to make a pH from 6.1 to 10.5, thereby preparing the solution containing the carbamic acid derivative of arbekacin including arbekacin carbonate.

3. The production method according to claim 1, wherein, in the step (a), any one of a carbonate and a hydrogen carbonate in an amount of 0.5 equivalents or more is added to the solution containing arbekacin free base, thereby preparing the solution containing the carbamic acid derivative of arbekacin including arbekacin carbonate.

4. The production method according to claim 1, wherein, in the step (b), the solution prepared in the step (a) is mixed with an organic solvent, thereby precipitating the carbamic acid derivative of arbekacin including arbekacin carbonate.

5. The production method according to claim 4, wherein the organic solvent used in the step (b) is selected from the group consisting of methanol, ethanol, propanol, dimethyl sulfoxide, acetonitrile, pyridine, tetrahydrofuran, acetone, N,N-dimethylformamide, and solvent combinations thereof.

6. A carbamic acid derivative of arbekacin including arbekacin carbonate, produced by the method according to claim 1.

7. A production method for arbekacin free base, the production method comprising:
(a) a step of adding any one of carbon dioxide, a carbonate, and a hydrogen carbonate to a solution containing arbekacin free base, thereby preparing a solution containing a carbamic acid derivative of arbekacin represented by the following formula (2):

Formula (2)

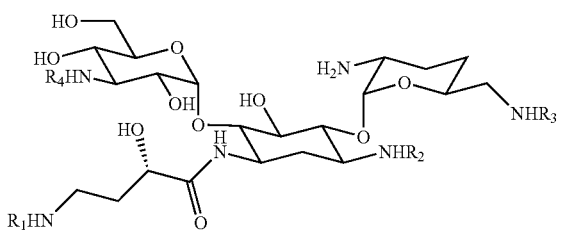

in the Formula (2), at least one of $R_1$, $R_2$, $R_3$, and $R_4$ is COOH, while the rest represent H including arbekacin carbonate represented by the following Formula (1):

Formula (1)

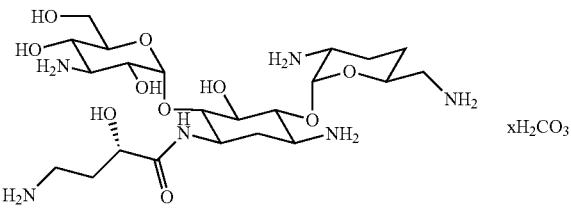

xH₂CO₃ in the Formula (1), x represents 1 to 5;
(b) a step of precipitating the carbamic acid derivative of arbekacin including arbekacin carbonate in the solution;
(c) a step of separating the precipitated carbamic acid derivative of arbekacin including arbekacin carbonate; and
(d) a step of removing carbon dioxide from the carbamic acid derivative of arbekacin including arbekacin carbonate obtained in the step (c).

8. A production method for a pharmaceutically acceptable salt of arbekacin represented by the following Formula (3):

Formula (3)

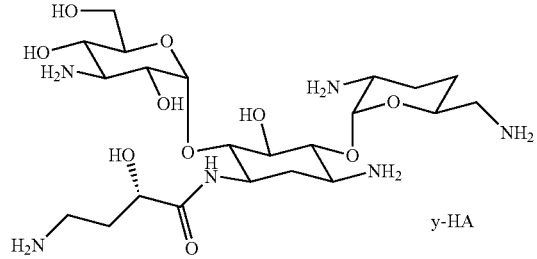

y·HA in the Formula (3), y represents 1 to 5, and HA represents a pharmaceutically acceptable acid, the production method comprising:
(a) a step of adding any one of carbon dioxide, a carbonate, and a hydrogen carbonate to a solution containing arbekacin free base, thereby preparing a solution containing a carbamic acid derivative of arbekacin represented by the following formula (2):

Formula (2)

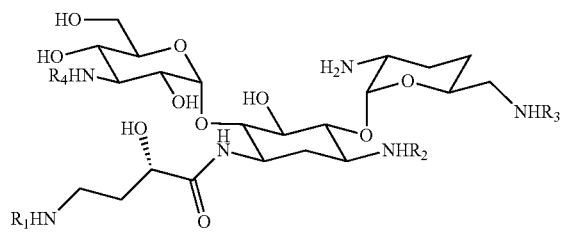

in the Formula (2), at least one of $R_1$, $R_2$, $R_3$, and $R_4$ is COOH, while the rest represents H including arbekacin carbonate represented by the following Formula (1):

Formula (1)

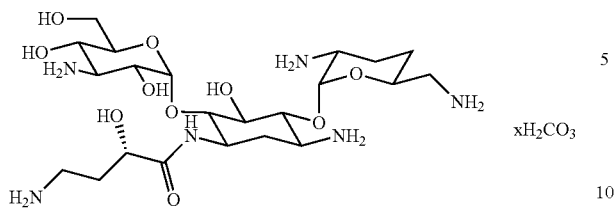

in the Formula (1), x represents 1 to 5:
- (b) a step of precipitating the carbamic acid derivative of arbekacin including arbekacin carbonate in the solution;
- (c) a step of separating the precipitated carbamic acid derivative of arbekacin including arbekacin carbonate; and
- (e) a step of adding an acid to the carbamic acid derivative of arbekacin including arbekacin carbonate obtained in the step (c).

\* \* \* \* \*